(12) United States Patent
Wang et al.

(10) Patent No.: US 6,728,599 B2
(45) Date of Patent: Apr. 27, 2004

(54) MODULARITY SYSTEM FOR COMPUTER ASSISTED SURGERY

(75) Inventors: Yulun Wang, Goleta, CA (US); Modjtaba Ghodoussi, Santa Barbara, CA (US); Darrin Uecker, Santa Barbara, CA (US); James Wright, Santa Barbara, CA (US); Amante Mangaser, Goleta, CA (US)

(73) Assignee: Computer Motion, Inc., Sunnyvale, CA (US)

( * ) Notice: Subject to any disclaimer, the term of this patent is extended or adjusted under 35 U.S.C. 154(b) by 0 days.

(21) Appl. No.: 09/949,050

(22) Filed: Sep. 7, 2001

(65) Prior Publication Data

US 2003/0050733 A1 Mar. 13, 2003

(51) Int. Cl.⁷ .......................... G05B 15/00; G05B 19/00
(52) U.S. Cl. .................. 700/258; 700/245; 700/246; 700/257; 700/259; 700/260; 600/102; 600/424; 600/427; 600/429; 600/595; 607/3; 607/9; 607/17; 128/897; 128/898; 128/923; 606/1; 606/130; 356/399; 379/88.14
(58) Field of Search ................................ 700/245, 257, 700/259, 258, 246, 260; 600/102, 427, 429, 595, 424; 606/130, 1; 128/897, 898, 923; 607/3, 9, 17; 356/399; 269/238, 297; 379/88.14; 414/1

(56) References Cited

U.S. PATENT DOCUMENTS

| 977,825 A | 12/1910 | Murphy |
|---|---|---|
| 3,171,549 A | 3/1965 | Orloff |
| 3,280,991 A | 10/1966 | Melton et al. |
| 4,058,001 A | 11/1977 | Waxman |
| 4,128,880 A | 12/1978 | Cray, Jr. |
| 4,221,997 A | 9/1980 | Flemming |
| 4,367,998 A | 1/1983 | Causer |
| 4,401,852 A | 8/1983 | Noso et al. |
| 4,456,961 A | 6/1984 | Price et al. |

(List continued on next page.)

FOREIGN PATENT DOCUMENTS

| DE | U 9204118.3 | 7/1992 |
|---|---|---|
| DE | 4310842 C2 | 1/1995 |
| EP | 0239409 A1 | 9/1987 |
| EP | 0424687 A1 | 5/1991 |
| EP | 0776738 A2 | 6/1997 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

Mack, Minimally invasive and robotic, 2001, Internet, pp. 568–572.*
Schaaf, Robotic surgery: The future is now, 2001, Internet, pp. 1–13.*
Noonan, NBC Newsweek, The ultimate remote control, 1999, Internet, pp. 1–11.*

(List continued on next page.)

Primary Examiner—William A. Cuchlinski, Jr.
Assistant Examiner—McDieunel Marc
(74) Attorney, Agent, or Firm—Townsend & Townsend & Crew LLP

(57) ABSTRACT

A medical system that allows a medical device to be controlled by one of two input devices. The input devices may be consoles that contain handles and a screen. The medical devices may include robotic arms and instruments used to perform a medical procedure. The system may include an arbitrator that determines which console has priority to control one or more of the robotic arms/instruments.

60 Claims, 7 Drawing Sheets

U.S. PATENT DOCUMENTS

| | | | |
|---|---|---|---|
| 4,460,302 A | 7/1984 | Moreau et al. | |
| 4,474,174 A | 10/1984 | Petruzzi | |
| 4,491,135 A | 1/1985 | Klein | |
| 4,503,854 A | 3/1985 | Jako | |
| 4,517,963 A | 5/1985 | Michel | |
| 4,523,884 A | 6/1985 | Clement et al. | |
| 4,586,398 A | 5/1986 | Yindra | |
| 4,604,016 A | 8/1986 | Joyce | |
| 4,616,637 A | 10/1986 | Caspari et al. | |
| 4,624,011 A | 11/1986 | Watanabe et al. | |
| 4,633,389 A | 12/1986 | Tanaka et al. | |
| 4,635,292 A | 1/1987 | Mori et al. | |
| 4,635,479 A | 1/1987 | Salisbury, Jr. et al. | |
| 4,641,292 A | 2/1987 | Tunnell et al. | |
| 4,655,257 A | 4/1987 | Iwashita | |
| 4,672,963 A | 6/1987 | Barken | |
| 4,676,243 A | 6/1987 | Clayman | |
| 4,728,974 A | 3/1988 | Nio et al. | |
| 4,762,455 A | 8/1988 | Coughlan et al. | |
| 4,791,934 A | 12/1988 | Brunnett | |
| 4,791,940 A | 12/1988 | Hirschfeld et al. | |
| 4,794,912 A | 1/1989 | Lia | |
| 4,815,006 A | 3/1989 | Andersson et al. | |
| 4,815,450 A | 3/1989 | Patel | |
| 4,837,734 A | 6/1989 | Ichikawa et al. | |
| 4,852,083 A | 7/1989 | Niehaus et al. | |
| 4,853,874 A | 8/1989 | Iwamoto et al. | |
| 4,854,301 A | 8/1989 | Nakajima | |
| 4,860,215 A | 8/1989 | Seraji | |
| 4,863,133 A | 9/1989 | Bonnell | |
| 4,883,400 A | 11/1989 | Kuban et al. | |
| 4,930,494 A | 6/1990 | Takehana et al. | |
| 4,945,479 A | 7/1990 | Rusterholz et al. | |
| 4,949,717 A | 8/1990 | Shaw | |
| 4,954,952 A | 9/1990 | Ubhayakar et al. | |
| 4,965,417 A | 10/1990 | Massie | |
| 4,969,709 A | 11/1990 | Sogawa et al. | |
| 4,969,890 A | 11/1990 | Sugita et al. | |
| 4,979,933 A | 12/1990 | Runge | |
| 4,979,949 A | 12/1990 | Matsen, III et al. | |
| 4,980,626 A | 12/1990 | Hess et al. | |
| 4,989,253 A | 1/1991 | Liang et al. | |
| 4,996,975 A | 3/1991 | Nakamura | |
| 5,019,968 A | 5/1991 | Wang et al. | |
| 5,020,001 A | 5/1991 | Yamamoto et al. | |
| 5,046,375 A | 9/1991 | Salisbury, Jr. et al. | |
| 5,065,741 A | 11/1991 | Uchiyama et al. | |
| 5,078,140 A | 1/1992 | Kwoh | |
| 5,086,401 A | 2/1992 | Glassman et al. | |
| 5,091,656 A | 2/1992 | Gahn | |
| 5,097,829 A | 3/1992 | Quisenberry | |
| 5,097,839 A | 3/1992 | Allen | |
| 5,098,426 A | 3/1992 | Sklar et al. | |
| 5,105,367 A | 4/1992 | Tsuchihashi et al. | |
| 5,109,499 A | 4/1992 | Inagami et al. | |
| 5,123,095 A | 6/1992 | Papadopoulos et al. | |
| 5,131,105 A | 7/1992 | Harrawood et al. | |
| 5,142,930 A | 9/1992 | Allen et al. | |
| 5,145,227 A | 9/1992 | Monford, Jr. | |
| 5,166,513 A | 11/1992 | Keenan et al. | |
| 5,175,694 A | 12/1992 | Amato | |
| 5,182,641 A | 1/1993 | Diner et al. | |
| 5,184,601 A | 2/1993 | Putman | |
| 5,187,574 A | 2/1993 | Kosemura et al. | |
| 5,196,688 A | 3/1993 | Hesse et al. | |
| 5,201,325 A | 4/1993 | McEwen et al. | |
| 5,201,743 A | 4/1993 | Haber et al. | |
| 5,217,003 A | * 6/1993 | Wilk | 700/131 |
| 5,221,283 A | 6/1993 | Chang | |
| 5,228,429 A | 7/1993 | Hatano | |
| 5,230,623 A | 7/1993 | Guthrie et al. | |
| 5,236,432 A | 8/1993 | Matsen, III et al. | |
| 5,251,127 A | 10/1993 | Raab | |
| 5,257,999 A | 11/1993 | Slanetz, Jr. | |
| 5,271,384 A | 12/1993 | McEwen et al. | |
| 5,279,309 A | 1/1994 | Taylor et al. | |
| 5,282,806 A | 2/1994 | Haber | |
| 5,289,273 A | 2/1994 | Lang | |
| 5,289,365 A | 2/1994 | Caldwell et al. | |
| 5,299,288 A | 3/1994 | Glassman et al. | |
| 5,300,926 A | 4/1994 | Stoeckl | |
| 5,303,148 A | 4/1994 | Mattson et al. | |
| 5,304,185 A | 4/1994 | Taylor | |
| 5,305,203 A | 4/1994 | Raab | |
| 5,305,427 A | 4/1994 | Nagata | |
| 5,309,717 A | 5/1994 | Minch | |
| 5,313,306 A | 5/1994 | Kuban et al. | |
| 5,320,630 A | 6/1994 | Ahmed | |
| 5,337,732 A | 8/1994 | Grundfest et al. | |
| 5,339,799 A | 8/1994 | Kami et al. | |
| 5,343,385 A | 8/1994 | Joskowicz et al. | |
| 5,343,391 A | 8/1994 | Mushabac | |
| 5,345,538 A | 9/1994 | Narayannan et al. | |
| 5,357,962 A | 10/1994 | Green | |
| 5,368,015 A | 11/1994 | Wilk | |
| 5,368,428 A | 11/1994 | Hussey et al. | |
| 5,371,536 A | 12/1994 | Yamaguchi | |
| 5,382,885 A | 1/1995 | Salcudean et al. | |
| 5,388,987 A | 2/1995 | Badoz et al. | |
| 5,395,369 A | 3/1995 | McBrayer et al. | |
| 5,397,323 A | 3/1995 | Taylor et al. | |
| 5,402,801 A | 4/1995 | Taylor | |
| 5,403,319 A | 4/1995 | Matsen, III et al. | |
| 5,408,409 A | 4/1995 | Glassman et al. | |
| 5,410,638 A | 4/1995 | Colgate et al. | |
| 5,417,210 A | 5/1995 | Funda et al. | |
| 5,417,701 A | 5/1995 | Holmes | |
| 5,422,521 A | 6/1995 | Neer et al. | |
| 5,431,645 A | 7/1995 | Smith et al. | |
| 5,434,457 A | 7/1995 | Josephs et al. | |
| 5,442,728 A | 8/1995 | Kaufman et al. | |
| 5,443,484 A | 8/1995 | Kirsch et al. | |
| 5,445,166 A | 8/1995 | Taylor | |
| 5,451,924 A | 9/1995 | Massimino et al. | |
| 5,455,766 A | 10/1995 | Hirschfeld et al. | |
| 5,458,547 A | 10/1995 | Teraoka et al. | |
| 5,458,574 A | 10/1995 | Machold et al. | |
| 5,476,010 A | 12/1995 | Fleming et al. | |
| 5,490,117 A | 2/1996 | Oda et al. | |
| 5,490,843 A | 2/1996 | Hildwein et al. | |
| 5,506,912 A | 4/1996 | Nagasaki et al. | |
| 5,512,919 A | 4/1996 | Araki | |
| 5,515,478 A | 5/1996 | Wang | |
| 5,544,654 A | 8/1996 | Murphy et al. | |
| 5,553,198 A | 9/1996 | Wang et al. | |
| 5,562,503 A | 10/1996 | Ellman et al. | |
| 5,571,110 A | 11/1996 | Matsen, III et al. | |
| 5,572,999 A | 11/1996 | Funda et al. | |
| 5,598,269 A | * 1/1997 | Kitaevich et al. | 700/132 |
| 5,609,560 A | * 3/1997 | Ichikawa et al. | 600/101 |
| 5,626,595 A | 5/1997 | Sklar et al. | |
| 5,629,594 A | 5/1997 | Jacobus et al. | |
| 5,630,431 A | 5/1997 | Taylor | |
| 5,631,973 A | 5/1997 | Green | |
| 5,636,259 A | 6/1997 | Khutoryansky et al. | |
| 5,649,956 A | 7/1997 | Jensen et al. | |
| 5,657,429 A | 8/1997 | Wang et al. | |
| 5,658,250 A | 8/1997 | Blomquist et al. | |
| 5,676,673 A | 10/1997 | Ferre et al. | |
| 5,695,500 A | 12/1997 | Taylor et al. | |
| 5,696,574 A | 12/1997 | Schwaegerle | |

| | | |
|---|---|---|
| 5,696,837 A | 12/1997 | Green |
| 5,718,038 A | 2/1998 | Takiar et al. |
| 5,727,569 A | 3/1998 | Benetti et al. |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,766,126 A | 6/1998 | Anderson |
| 5,776,126 A | 7/1998 | Wilk et al. |
| 5,779,623 A | 7/1998 | Bonnell |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,827,319 A | 10/1998 | Carlson et al. |
| 5,836,869 A | 11/1998 | Kudo et al. |
| 5,844,824 A | 12/1998 | Newman et al. |
| 5,855,583 A | 1/1999 | Wang et al. |
| 5,859,934 A | 1/1999 | Green |
| 5,860,995 A | 1/1999 | Berkelaar |
| 5,871,017 A * | 2/1999 | Mayer ................... 128/897 |
| 5,876,325 A | 3/1999 | Mizuno et al. |
| 5,878,193 A | 3/1999 | Wang et al. |
| 5,882,206 A | 3/1999 | Gillio |
| 5,887,121 A | 3/1999 | Funda et al. |
| 5,898,599 A | 4/1999 | Massie et al. |
| 5,904,702 A | 5/1999 | Ek et al. |
| 5,906,630 A | 5/1999 | Anderhub et al. |
| 5,911,036 A | 6/1999 | Wright et al. |
| 5,920,395 A | 7/1999 | Schultz |
| 5,931,832 A | 8/1999 | Jensen |
| 5,950,629 A | 9/1999 | Taylor et al. |
| 5,951,475 A | 9/1999 | Gueziec et al. |
| 5,951,587 A | 9/1999 | Qureshi et al. |
| 5,954,731 A | 9/1999 | Yoon |
| 5,957,902 A | 9/1999 | Teves |
| 5,967,980 A * | 10/1999 | Ferre et al. ................ 600/424 |
| 5,971,976 A * | 10/1999 | Wang et al. ................ 700/258 |
| 5,980,782 A | 11/1999 | Hershkowitz et al. |
| 5,984,932 A | 11/1999 | Yoon |
| 6,006,127 A * | 12/1999 | Van Der Brug et al. .... 600/427 |
| 6,024,695 A | 2/2000 | Taylor et al. |
| 6,080,181 A | 6/2000 | Jensen et al. |
| 6,106,511 A | 8/2000 | Jensen |
| 6,120,433 A | 9/2000 | Mizuno et al. |
| 6,132,368 A | 10/2000 | Cooper |
| 6,201,984 B1 | 3/2001 | Funda et al. |
| 6,206,903 B1 | 3/2001 | Ramans |
| 6,223,100 B1 | 4/2001 | Green |
| 6,226,566 B1 | 5/2001 | Funda et al. |
| 6,231,526 B1 | 5/2001 | Taylor et al. |
| 6,246,200 B1 | 6/2001 | Blumenkranz et al. |
| 6,259,806 B1 | 7/2001 | Green |
| 6,309,397 B1 | 10/2001 | Julian et al. |
| 6,312,435 B1 | 11/2001 | Wallace et al. |
| 6,331,181 B1 | 12/2001 | Tierney et al. |
| 6,346,072 B1 | 2/2002 | Cooper |
| 6,364,888 B1 | 4/2002 | Nieneyer et al. |
| 6,368,332 B1 * | 4/2002 | Salcudean et al. .......... 606/130 |
| 6,371,952 B1 | 4/2002 | Madhani et al. |
| 6,490,490 B1 | 12/2002 | Uchikubo et al. |

OTHER PUBLICATIONS

Rotmes et al., Digital trainer developed for robotic assisted cardiac surgery, no date, Internet, pp. 1–7.*
Butner et al., A real–time system for tele–surgery, 2001, Internet, pp. 236–243.*
Lai et al., Evaluating control modes for constrained robotic surgery, 2000, Internet, pp. 1–7.*
Cavusoglu et al., A laparoscopic telesurgical workstation, 1999, IEEE/Internet, pp. 728–739.*
Lapietra et al., Will surgeons of the "Computer–game generation" Have an advantage in developing robotic skills?, 2001, Internet, pp. 26–30.*
SVI, Minimally invasive surgery, 1998, Internet, pp. 1–4.*
Howe et al., Robotics for surgery, 1999, Internet, pp. 211–242.*
Willet, Telesurgery, 2001, Internet, pp. 1–3.*
Richard, Emerging technologies for surgery in the $21^{st}$ century, 1999, Internet, pp. 1–9.*
Parsell, Surgeons in U.S. perform operation on France via robot, 2001, Internet, pp. 1–5.*
"Endocorporeal Surgery Using Remote Manipulators"(Ned S. Rasor and J.W. Spickler) Remotely Manned Systems—Exploration and Operation in Space, California Institute of Technology 1973.
"A Survey Study of Teleoperators, Robotics, and Remote Systems Technology" (Arthur D. Alexander, III) Remotely Manned Systems—Exploration and Operation in Space, California Institute of Technology 1973.
"Impacts of Telemation on Modern Society" (Arthur D. Alexander, III), On the Theory and Practice of Robots and Manipulators vol. II, 1974.
Transcript of a video presented by SRI at the 3rd World Congress of Endoscopic Surgery in Bordeaux on Jun. 18–20, 1992, in Washington on Apr. 9, 1992, and in San Diego, CA on Jun. 4–7, 1992 entitled "Telepresence Surgery—The Future of Minimally Invasive Medicine".
Statutory Declaration of Dr. Phillip S. Green, presenter of the video entitled "Telepresence Surgery—Teh Future of Minimally Invasive Medicine".
Abstract of a presentation "Telepresence: Advanced Teleoperator Technology for Minimally Invasive Surgery" (P. Green et al.) given at the 3rd World Congress of Endoscopic Surgery in Bordeaux, Jun. 18–20, 1992.
Abstract of a presentation "Telepresence: Advanced Teleoperator Technology for Minimally Invasive Surgery", (P. Green et al.) given at "Medicine meets virtual reality" symposium in San Diego, Jun. 4–7, 1992.
Abstract of a presentation "Camera Control for Laparoscopic Surgery by Speech–Recognizing Robot: Constant Attention and Better Use of Personnel" (Colin Besant et al.) given at the 3rd World Congress of Endoscopic Surgery in Bordeaux, Jun. 18–20, 1992.
"A Literature Review: Robots in Medicine" (B. Preising et al.) IEEE June 1991.
"Robots for the Operating Room" (Elizabeth Corcoran), The New York Times, Sunday Jul. 19, 1992, Section 3, p. 9, Column 1.
"Taming the Bull: Safety in a Precise Surgical Robot"(Russell H. Taylor et al.), IEEE 1991.
Abstract of a presentation "Design Considerations of a New Generation Endoscope Using Robotics and Computer Vision Technology" (S.M. Krishnan et al.) given at the 3rd World Congress of Endoscopic Surgery in Bordeaux, Jun. 18–20, 1992.

Abstract of a presentation "3–D vision Technology Applied to Advanced Minimally Invasive Surgery Systems" given at the 3rd World Congress of Endoscopic Surgery in Bordeaux, Jun. 18–20, 1992.

"Analysis of the Surgeon's Grasp for Telerobotic Surgical Manipulation" (Frank Tendick and Lawrence Stark), IEEE 1989.

"Kinematic Control and Visual Display of Redundant Teleoperators"(Hardi Das et al.), IEEE 1989.

"A New System for Computer Assisted Neurosurgery" (S. Lavallee), IEEE 1989.

"An Advanced Control Micromanipulator for Surgical Applications" (Ben Gayed et al.), Systems Science vol. 13 1987.

"Force Feedback–Based Telemicromanipulation for Robot Surgery on Soft Tissue" (A.M. Sabatini et al.), IEEE 1989.

"Six–Axis Bilateral Control of an Articulated Slave Manipulator Using a Cartesian Master Manipulator" (Masao Inoue), Advanced Robotics 1990.

"On a Micro–Manipulator for Medical Application—Stability Consideration of its Bilateral Controller" (S. Majima et al.), Mechatronics 1991.

"Anthropomorphic Remote Manipulator", NASA Tech Briefs 1991.

"Controlling Remote Manipulators through Kinesthetic Coupling" (A.K. Bejczy), Computers in Mechanical Engineering 1983.

"Design of a Surgeon–Machine Interface for Teleoperated Microsurgery" (Steve Charles M.D. et al.), IEEE 1989.

"A Robot in an Operating Room: A Bull in a China Shop" (J.M. Dolan et al.), IEEE 1987.

Abstract of a presentation "Concept and Experimental Application of a Surgical Robotic System the Steerable MIS Instrument SMI" given at the 3rd World Congress of Endoscopic Surgery in Bordeaux, Jun. 18–20, 1992.

Abstract of a presentaion given at the 3rd World Congress of Endoscopic Surgery in Bordeaux, Jun. 18–20, 1992, entitled "Session 15/1".

Abstract of a presentation "A Pneumatic Controlled Sewing Device for Endoscopic Application the MIS Sewing Instrument MSI" given at the 3rd World Congress of Endoscopic Surgery in Bordeaux, Jun. 18–20, 1992.

Abstract of a presentation given at the 3rd World Congress of Endoscopic Surgery in Bordeaux (Jun. 18–20, 1992), entitled "Session 15/2".

Abstract of a presentation given at the 3rd World Congress of Endoscopic Surgery in Bordeaux (Jun. 18–20, 1992), entitled Session 15/4.

Abstract of a presentation given at the 3rd World Congress of Endoscopic Surgery in Bordeaux (Jun. 18–20, 1992), entitled "Session 15/5".

"Properties of Master–Slave Robots" (C. Vibet), Motor–con 1987.

"A New Microsurgical Robot System for Corneal Transplantation" (Noriyuki Tejima), Precision Machinery 1988.

"Human/Robot Interaction via the Transfer of Power and Information Signals—Part I: Dynamics and Control Analysis" (H. Kazerooni), IEEE 1989.

"Human/Robot Interaction via the Transfer of Power and Information Signals—Part II: An Experimental Analysis" (H. Kazerooni), IEEE 1989.

"Power and Impedance Scaling in Bilateral Manipulation" (J. Edward Colgate), IEEE 1991.

"S.M.O.S.: Stereotaxical Microtelemanipulator for Ocular Surgery" (Aicha Guerrouad and Pierre Vidal), IEEE 1989.

"Motion Control for a Sheep Shearing Robot" (James P. Trevelyan et al.), Proceedings of the 1st International Symposium on Robotics Research, MIT, Cambridge, Massachusetts, USA, 1983.

"Robots and Telechirs" (M.W. Thring), Wiley 1983.

Industrial Robotics (Gordon M. Mair), Prentice Hall 1988 (pp. 41–43, 49–50, 54, 203–209 enclosed).

"Student Reference Manual for Electronic Instrumentation Laboratories" (Wolf et al.), Prentice Hall, New Jersey 1990, pp. 498 amd 499.

"Surgery in Cyberspace" (Taubes), Discover Magazine, Dec. 1994.

* cited by examiner

MODULARITY SYSTEM FOR COMPUTER ASSISTED SURGERY

BACKGROUND OF THE INVENTION

1. Field of the Invention

The present invention relates to a medical robotic system.

2. Background Information

Blockage of a coronary artery may deprive the heart of blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery is then severed and attached to the artery at the point of incision. The internal mammary artery bypasses the blocked area of the artery to again provide a full flow of blood to the heart. Splitting the sternum and opening the chest cavity can create a tremendous trauma to the patient. Additionally, the cracked sternum prolongs the recovery period of the patient.

Computer Motion of Goleta, Calif. provides a system under the trademark ZEUS that allows a surgeon to perform a minimally invasive CABG procedure. The procedure is performed with instruments that are inserted through small incisions in the patient's chest. The instruments are controlled by robotic arms. Movement of the robotic arms and actuation of instrument end effectors are controlled by the surgeon through a pair of handles and a foot pedal that are coupled to an electronic controller. Alternatively, the surgeon can control the movement of an endoscope used to view the internal organs of the patient through voice commands.

The handles and a screen are typically integrated into a console that is operated by the surgeon to control the various robotic arms and medical instruments of a ZEUS system. Utilizing a robotic system to perform surgery requires a certain amount of training. It would be desirable to provide a system that would allow a second surgeon to assist another surgeon in controlling a robotic medical system. The second surgeon could both teach and assist a surgeon learning to perform a medical procedure with a ZEUS system. This would greatly reduce the time required to learn the operation of a robotically assisted medical system.

U.S. Pat. No. 5,217,003 issued to Wilk discloses a surgical system which allows a surgeon to remotely operate robotically controlled medical instruments through a telecommunication link. The Wilk system only allows for one surgeon to operate the robotic arms at a given time. Wilk does not disclose or contemplate a system which allows two different surgeons to operate the same set of robotic arms.

U.S. Pat. No. 5,609,560 issued to Ichikawa et al. and assigned to Olympus Optical Co. Ltd. discloses a system that allows an operator to control a plurality of different medical devices through a single interface. The Olympus patent does not disclose a system which allows multiple input devices to control a single medical device.

BRIEF SUMMARY OF THE INVENTION

A medical system that includes a single medical device that can be controlled by one of two input devices.

DETAILED DESCRIPTION

Figure 1:
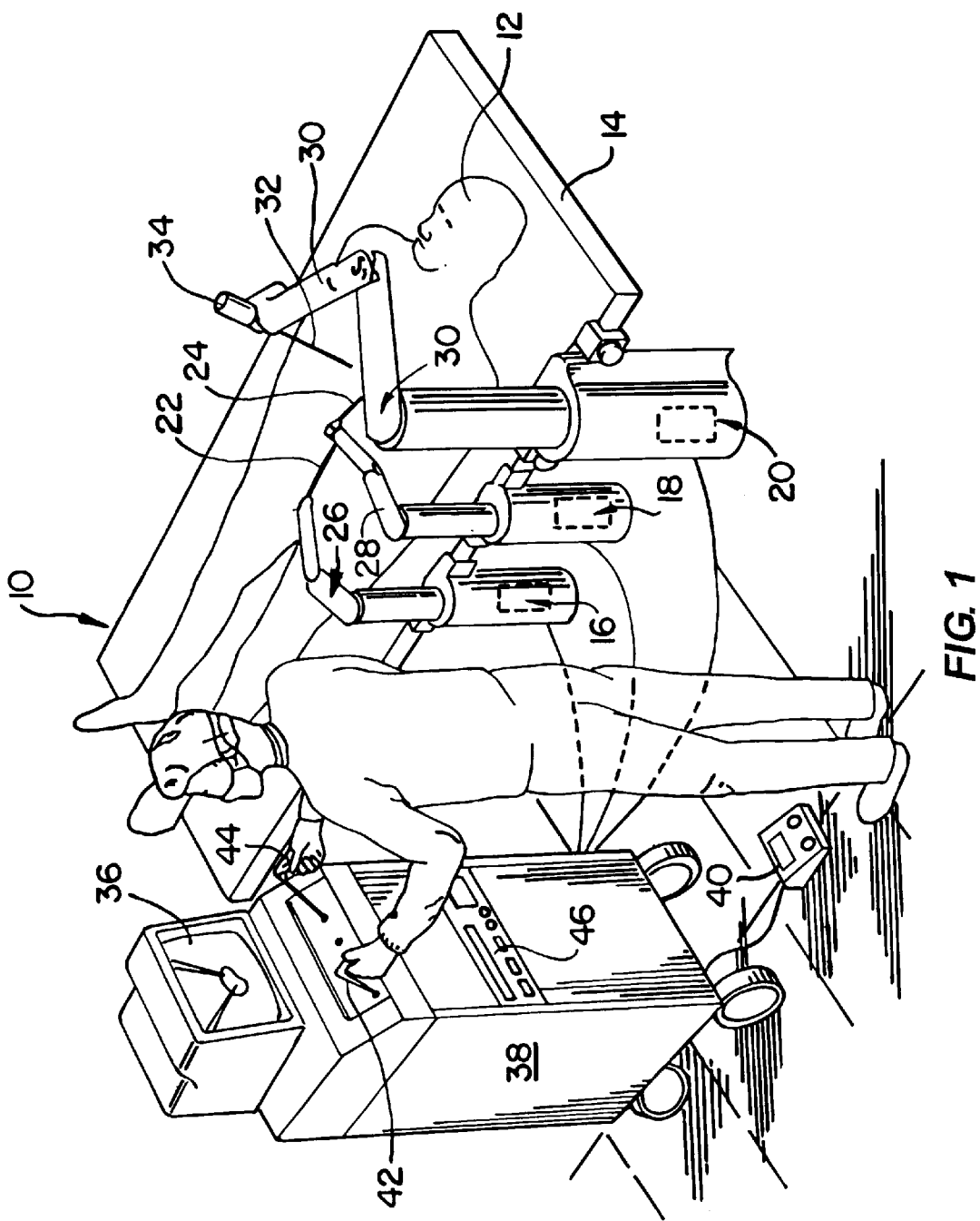
FIG. 1 is a perspective view of a medical robotic system.

Referring to the drawings more particularly by reference numbers, FIG. 1 shows a system 10 that can perform minimally invasive surgery. In one embodiment, the system 10 is used to perform a minimally invasive coronary artery bypass graft (MI-CABG) and other anastomostic procedures. Although a MI-CABG procedure is shown and described, it is to be understood that the system may be used for other surgical procedures. For example, the system can be used to suture any pair of vessels. The system 10 can be used to perform a procedure on a patient 12 that is typically lying on an operating table 14. Mounted to the operating table 14 is a first articulate arm 16, a second articulate arm 18 and a third articulate arm 20. The articulate arms 16, 18 and 20 are preferably mounted to the table 14 so that the arms are at a same reference plane as the patient. Although three articulate arms are shown and described, it is to be understood that the system may have any number of arms.

The first and second articulate arms 16 and 18 each have a surgical instrument 22 and 24, respectively, coupled to robotic arms 26 and 28, respectively. The third articulate arm 20 includes a robotic arm 30 that holds and moves an endoscope 32. The instruments 22 and 24, and endoscope 32 are inserted through incisions cut into the skin of the patient. The endoscope has a camera 34 that is coupled to a television monitor 36 which displays images of the internal organs of the patient.

The first 16, second 18, and third 20 articulate arms are coupled to a controller 38 which can control the movement of the arms. The controller 38 is connected to an input device 40 such as a foot pedal that can be operated by a surgeon to move the location of the endoscope 32. The controller 38 contains electrical circuits, such as a processor, to control the robotic arms 26, 28 and 30. The surgeon can view a different portion of the patient by depressing a corresponding button (s) of the pedal 40. The controller 38 receives the input signal(s) from the foot pedal 40 and moves the robotic arm 30 and endoscope 32 in accordance with the input commands of the surgeon. The robotic arm may be a device that is sold by the assignee of the present invention, Computer Motion, Inc. of Goleta, Calif., under the trademark AESOP. The system is also described in U.S. Pat. No. 5,657,429 issued to Wang et al., which is hereby incorporated by reference. Although a foot pedal 40 is shown and described, it is to be understood that the system may have other input means such as a hand controller, or a speech recognition interface.

The instruments 22 and 24 of the first 16 and second 18 articulate arms, respectively, are controlled by a pair of master handles 42 and 44 that can be manipulated by the surgeon. The handles 42 and 44, and arms 16 and 18, have a master-slave relationship so that movement of the handles 42 and 44 produces a corresponding movement of the surgical instruments 22 and 24. The handles 42 and 44 may be mounted to a portable cabinet 46. The handles 42 and 44 are also coupled to the controller 38.

The controller 38 receives input signals from the handles 42 and 44, computes a corresponding movement of the surgical instruments, and provides output signals to move the robotic arms 26 and 28 and instruments 22 and 24. The entire system may be a product marketed by Computer Motion under the trademark ZEUS. The operation of the system is also described in U.S. Pat. No. 5,762,458 issued to Wang et al. and assigned to Computer Motion, which is hereby incorporated by reference.

Figure 2:
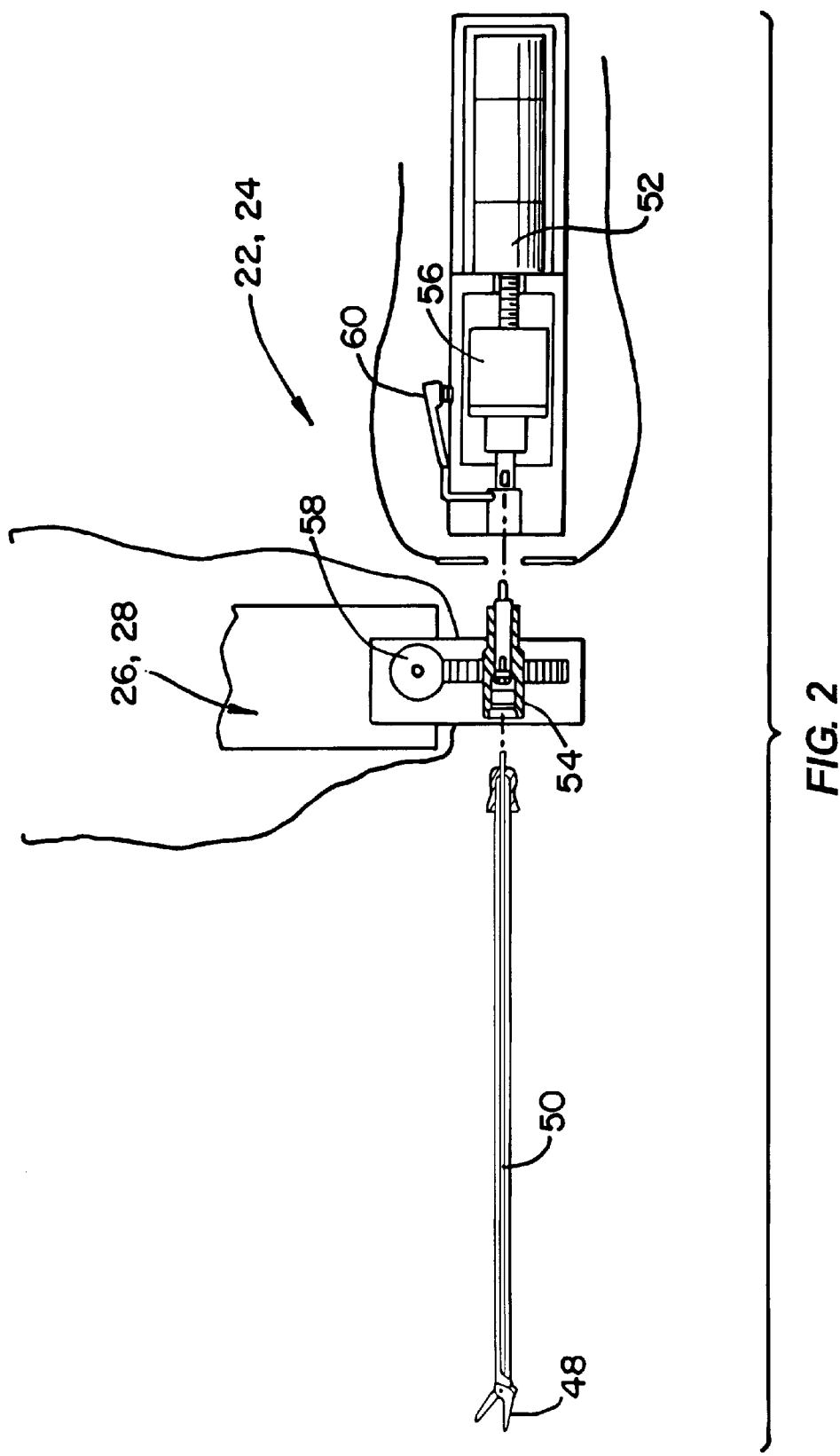
FIG. 2 is an exploded side view of an instrument of the robotic system.

FIG. 2 shows one of the surgical instruments 22 or 24. The instrument 22 or 24 includes an end effector 48 that is coupled to an actuator rod 50. The actuator rod 50 is coupled to a motor 52 by an adapter 54. The motor 52 actuates the end effector 48 by moving the actuator rod 50. The actuator rod 50 is coupled to a force sensor 56 that can sense the force being applied by the end effector 48. The force sensor 56 provides an analog output signal that is sent to the controller shown in FIG. 1.

The adapter 54 is coupled to a gear assembly 58 located at the end of a robotic arm 26 or 28. The gear assembly 58 can rotate the adapter 54 and end effector 48. The actuator rod 50 and end effector 48 may be coupled to the force sensor 56 and motor 52 by a spring biased lever 60. The instrument 22 or 24 may be the same or similar to an instrument described in the '458 patent.

Figure 3:
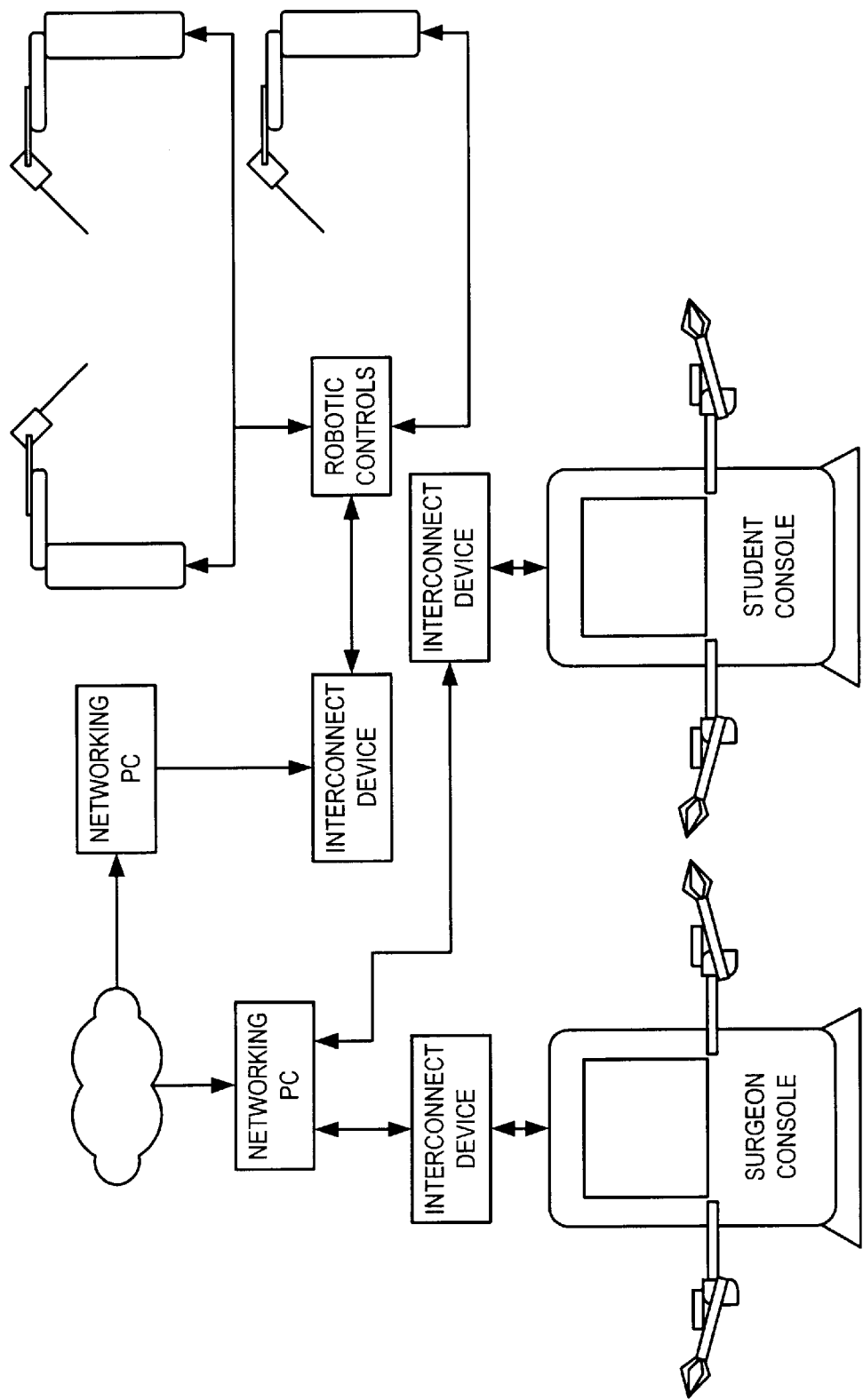
FIG. 3 is an illustration of network system.

FIG. 3 shows a system 100 that allows two different input devices to control one medical device. The input devices may be a first console 102 and a second console 104. The consoles 102 and 104 may each include the screen 36, handles 42 and 44, foot pedal (not shown) and controller 38 shown in FIG. 1. The medical devices may include the robotic arms 26, 28 and 30 and/or instruments 22 and 24 shown in FIG. 1. In general, the system allows a surgeon at either console 102 or 104 to control a medical device 22, 24, 26, 28 and or 30. For example, the surgeon at console 102 can move the robotic arms 26 and 28 through movement of the handles 42 and 44. The surgeon at console 104 can override the input from console 102 and control the movement of the robotic arms 26 and 28 through the movement of the console handles.

The consoles 102 and 104 are coupled to a network port 106 by a pair of interconnect devices 108 and 110. The network port 106 may be a computer that contains the necessary hardware and software to transmit and receive information through a communication link 112 in a communication network 114.

Consoles 102 and 104 provided by Computer Motion under the ZEUS mark provide output signals that may be incompatible with a computer. The interconnect devices 108 and 110 may provide an interface that conditions the signals for transmitting and receiving signals between the consoles 102 and 104 and the network computer 106.

It is to be understood that the computer and/or consoles 102 and 104 may be constructed so that the system does not require the interconnect devices 108 and 110. Additionally, the consoles 102 and 104 may be constructed so that the system does not require a separate networking computer 106. For example, the consoles 102 and 104 may be constructed and/or configured to directly transmit information through the communication network 114.

The system 100 may include a second network port 116 that is coupled to a device controller(s) 118 and the communication network 114. The device controller 118 controls the robotic arms 26, 28 and 30 and instruments 22 and 24. The second network port 116 may be a computer that is coupled to the controller 118 by an interconnect device 120. Although an interconnect device 120 and network computer 116 are shown and described, it is to be understood that the controller 118 can be constructed and configured to eliminate the device 120 and/or computer 116.

The communication network 114 may be any type of communication system including but not limited to, the internet and other types of wide area networks (WANs), intranets, local area networks (LANs), public switched telephone networks (PSTN), integrated services digital networks (ISDN). It is preferable to establish a communication link through a fiber optic network to reduce latency in the system. Depending upon the type of communication link selected, by way of example, the information can be transmitted in accordance with the user datagram protocol/internet protocol (UDP/IP) or ATM ADAPTION LAYER 1 (ATM/AAL1) protocols. The computers 112 and 116 may operate in accordance with an operating system sold under the designation VxWORKS by Wind River. By way of example, the computers 112 and 116 may be constructed and configured to operate with 100-base T Ethernet and/or 155 Mbps fiber ATM systems.

Figure 4:
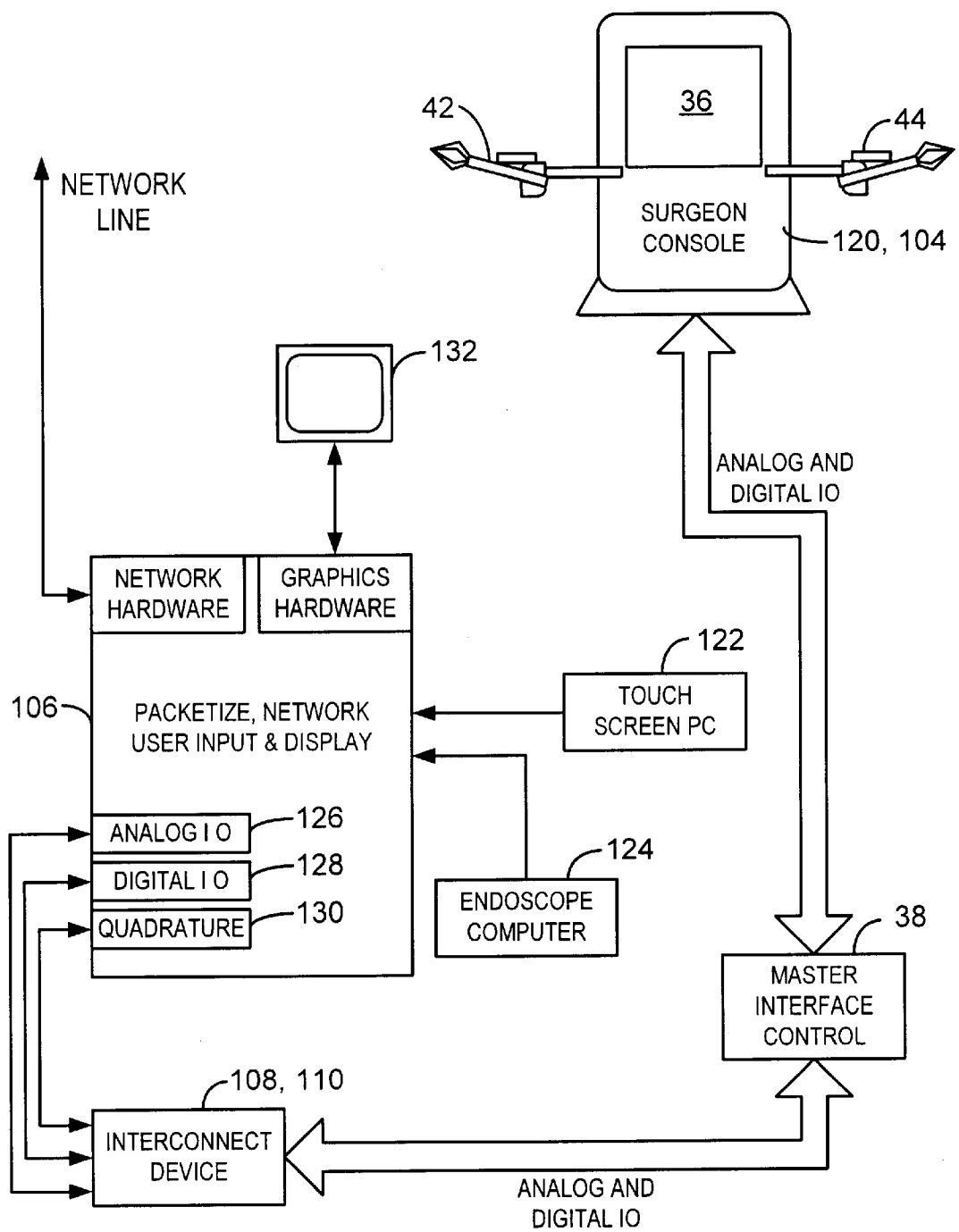
FIG. 4 is an illustration of a "surgeon" side of the system.

FIG. 4 shows an embodiment of a "surgeon" side of the system. Each console 102 and 104 may be accompanied by a touchscreen computer 122 and an endoscope interface computer 124. The touchscreen computer 122 may be a device sold by Computer Motion under the trademark HERMES. The touchscreen 122 allows the surgeon to control and vary different functions and operations of the instruments 22 and 24. For example, the surgeon may vary the scale between movement of the handles 42 and 44 and movement of the instruments 22 and 24 through a graphical user interface (GUI) of the touchscreen 122. The touchscreen 122 may have another GUI that allows the surgeon to initiate an action such as closing the gripper of an instrument.

The endoscope computer 124 may allow the surgeon to control the movement of the robotic arm 30 and the endoscope 32 shown in FIG. 1. The endoscope computer 124 may be an alternate to, or in addition to, the foot pedal 40 shown in FIG. 1. The endoscope computer 124 may be a device sold by Computer Motion under the trademark SOCRATES The touchscreen 122 and endoscope computers 124 may be coupled to the network computer 106 by RS232 interfaces.

A ZEUS console will transmit and receive information that is communicated as analog, digital or quadrature signals. The network computer 112 may have analog input/output (I/O) 126, digital I/O 128 and quadrature 130 interfaces that allow communication between the console 102 or 104 and the network 114. By way of example, the analog interface 126 may transceive data relating to handle position, tilt position, in/out position and foot pedal information (if used). The quadrature signals may relate to roll and pan position data. The digital I/O interface 128 may relate to cable wire sensing data, handle buttons, illuminators (LEDs) and audio feedback (buzzers). The position data is preferably absolute position information. By using absolute position information the robotic arms can still be moved even when some information is not successfully transmitted across the network 114. If incremental position information is provided, an error in the transmission would create a gap in the data and possibly inaccurate arm movement. The network computer 112 may further have a screen 132 that allows for a user to operate the computer 112.

Figure 5:
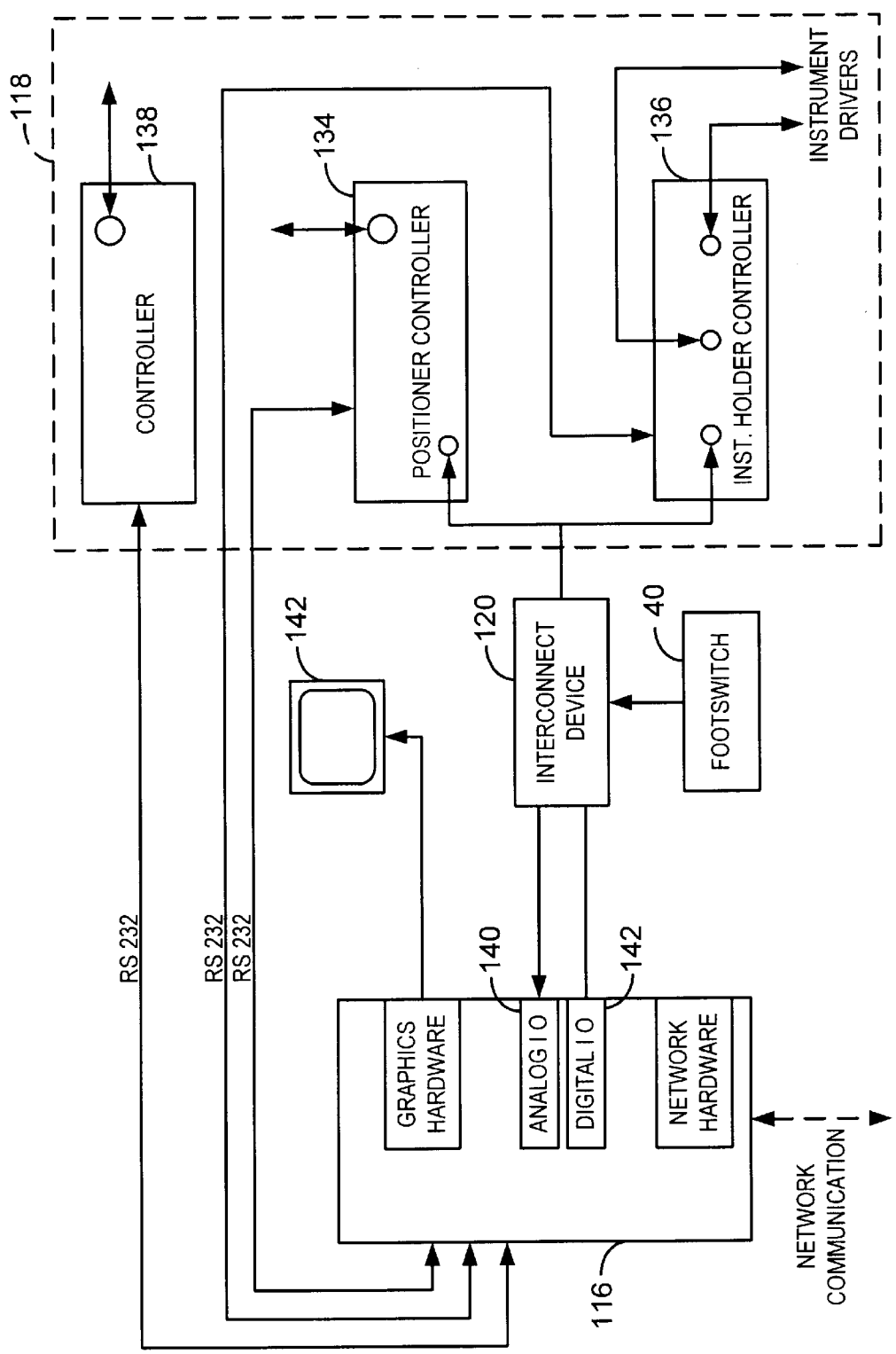
FIG. 5 is an illustration of a "patient" side of the system.

FIG. 5 shows an embodiment of a "patient" side of the system 100. The controller 118 may include three separate controllers 134, 136 and 138. The controller 134 may receive input commands, perform kinematic computations based on the commands, and drive output signals to move the robotic arms 26 and 28 and accompanying instruments 22 and 24 to a desired position. The controller 136 may receive commands that are processed to both move and actuate the instruments 22 and 24. Controller 138 may receive input commands, perform kinematic computations based on the commands, and drive output signals to move the robotic arm 30 and accompanying endoscope 32.

Controllers 134 and 136 may be coupled to the network computer 116 by digital I/O 140 and analog I/O 142 interfaces. The computer 116 may be coupled to the controller 138 by an RS232 interface. Additionally, the computer 116 may be coupled to corresponding RS232 ports of the controllers 134 and 136. The RS232 ports of the controllers 134 and 136 may receive data such as movement scaling and end effector actuation.

The robotic arms and instruments contain sensors, encoders, etc. that provide feedback information. Some or all of this feedback information may be transmitted over the network 114 to the surgeon side of the system. By way of example, the analog feedback information may include handle feedback, tilt feedback, in/out feedback and foot pedal feedback. Digital feedback may include cable sensing, buttons, illumination and audatory feedback. The computer 116 may be coupled to a screen 142.

The computers 106 and 116 may packetize the information for transmission through the communication network 114. Each packet will contain two types of data, robotic data and RS232 data. Robotic data may include position information of the robots, including input commands to move the robots and position feedback from the robots. RS232 data may include functioning data such as instrument scaling and actuation.

Because the system transmits absolute position data the packets of robotic data can be received out of sequence. This may occur when using a UDP/IP protocol which uses a best efforts methodology. The computers 106 and 116 are constructed and configured to disregard any "late" arriving packets with robotic data. For example, the computer 106 may transmits packets 1, 2 and 3. The computer 116 may receive the packets in the order of 1, 3 and 2. The computer 116 will disregard the second packet 2. Disregarding the packet instead of requesting a re-transmission of the data reduces the latency of the system. It is desirable to minimize latency to create a "real time" operation of the system.

It is preferable to have the RS232 information received in strict sequential order. Therefore the receiving computer will request a re-transmission of RS232 data from the transmitting computer if the data is not errorlessly received. RS232 data such as motion scaling and instrument actuation must be accurately transmitted and processed to insure that there is not an inadvertent command.

The computers 106 and 116 can multiplex the RS232 data from the various input sources. The computers 106 and 116 may have first-in first-out queues (FIFO) for transmitting information. Data transmitted between the computer 106 and the various components within the surgeon side of the system may be communicated through a protocol provided by Computer Motion under the name HERMES NETWORK PROTOCOL (HNP). Likewise, information may be transmitted between components on the patient side of the system in accordance with HNP.

In addition to the robotic and RS232 data, the patient side of the system will transmit video data from the endoscope camera 34. To reduce latency in the system, the computer 116 can multiplex the video data with the robotic/RS232 data onto the communication network. The video data may be compressed using conventional JPEG, etc. compression techniques for transmission to the surgeon side of the system.

Figure 6:
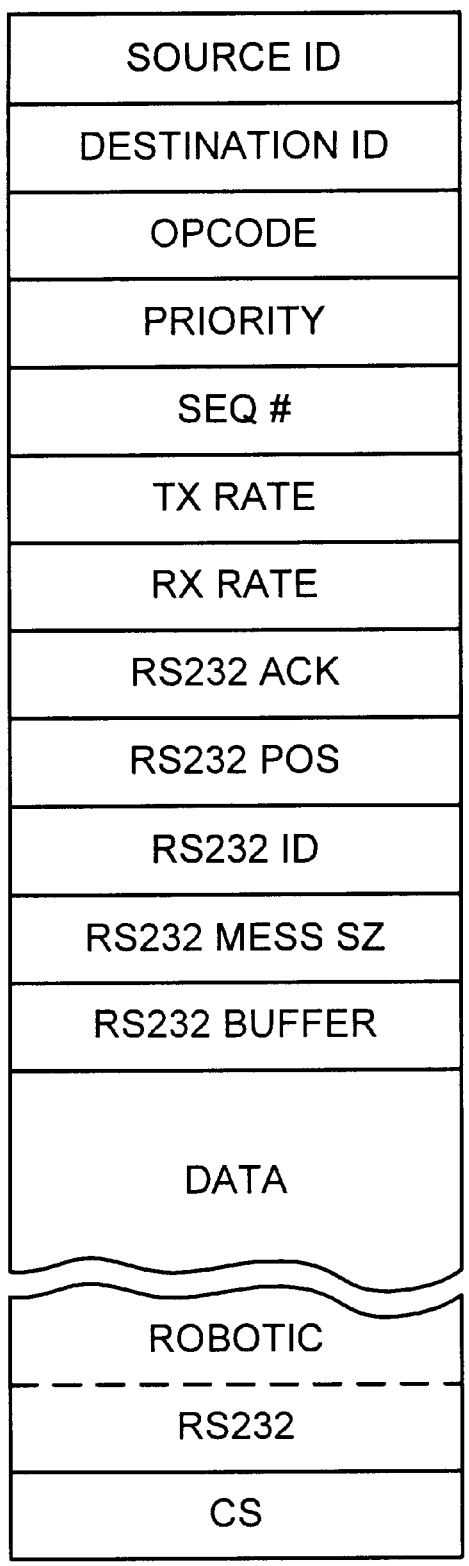
FIG. 6 is a schematic showing various fields of a packet transmitted across a communication network.

Each packet 150 may have the fields shown in FIG. 6. The SOURCE ID field includes identification information of the input device or medical device from where the data originates. The DESTINATION ID field includes identification information identifying the input device or medical device that is to receive the data. The OPCODE field defines the type of commands being transmitted. The PRIORITY field defines the priority of the input device. The priority data may be utilized to determine which input device has control of the medical device. The SEQ # field provides a packet sequence number so that the receiving computer can determine whether the packet is out of sequence.

The TX Rate field is the average rate at which packets are being transmitted. The RX Rate field is the average rate that packets are being received. The RS232 ACK field includes an acknowledgement count for RS232 data. RS232 data is typically maintained within the queue of a computer until an acknowledgement is received from the receiving computer that the data has been received.

The RS232 POS field is a counter relating to transmitted RS232 data. The RS232 ID field is an identification for RS232 data. The RS232 MESS SZ field contains the size of the packet. The RS232 BUFFER field contains the content length of the packet. The DATA field contains data being transmitted and may contain separate subfields for robotic and RS232 data. CS is a checksum field used to detect errors in the transmission of the packet.

Either computer 106 or 116 can be used as an arbitrator between the input devices and the medical devices. For example, the computer 116 may receive data from both consoles 102 and 104. The packets of information from each console 102 and 104 may include priority data in the PRIORITY fields. The computer 116 will route the data to the relevant device (eg. robot, instrument, etc.) in accordance with the priority data. For example, console 104 may have a higher priority than console 102. The computer 116 will route data to control a robot from console 104 to the exclusion of data from console 102 so that the surgeon at 104 has control of the arm.

As an alternate embodiment, the computer 116 may be constructed and configured to provide priority according to the data in the SOURCE ID field. For example, the computer 116 may be programmed to always provide priority for data that has the source ID from console 104. The computer 116 may have a hierarchical tree that assigns priority for a number of different input devices.

Alternatively, the computer 106 may function as the arbitrator, screening the data before transmission across the network 114. The computer 106 may have a priority scheme that always awards priority to one of the consoles 102 or 104. Additionally, or alternatively, one or more of the consoles 102 and 104 may have a mechanical and/or software switch that can be actuated to give the console priority. The switch may function as an override feature to allow a surgeon to assume control of a procedure.

In operation, the system initial performs a start-up routine. The ZEUS system is typically configured to start-up with data from the consoles. The consoles may not be in communication during the start-up routine of the robotic arms, instruments, etc. during the start-up routine so that the system does not have the console data required for system boot. The computer 116 may automatically drive the missing console input data to default values. The default values allow the patient side of the system to complete the start-up routine. Likewise, the computer 106 may also drive missing incoming signals from the patient side of the system to default values to allow the consoles 102 and/or 104 to boot-up. Driving missing signals to a default value may be part of a network local mode. The local mode allows one or more consoles to "hot plug" into the system without shutting the system down.

Additionally, if communication between the surgeon and patient sides of the system are interrupted during operation the computer 106 will again force the missing data to default values. The default values may be quiescent signal values to prevent unsafe operation of the system. The components on the patient side will be left at the last known value so that the instruments and arms do not move.

Once the start-up routines have been completed and the communication link has been established the surgeons can operate the consoles. The system is quite useful for medical procedures wherein one of the surgeons is a teacher and the other surgeon is a pupil. The arbitration function of the system allows the teacher to take control of robot movement and instrument actuation at anytime during the procedure. This allows the teacher to instruct the pupil on the procedure and/or the use of a medical robotic system.

Additionally, the system may allow one surgeon to control one medical device and another surgeon to control the other device. For example, one surgeon may move the instruments 22 and 24 while the other surgeon moves the endoscope 32, or one surgeon may move one instrument 22 or 24 while the other surgeon moves the other instrument 24 or 22.

Figure 7:
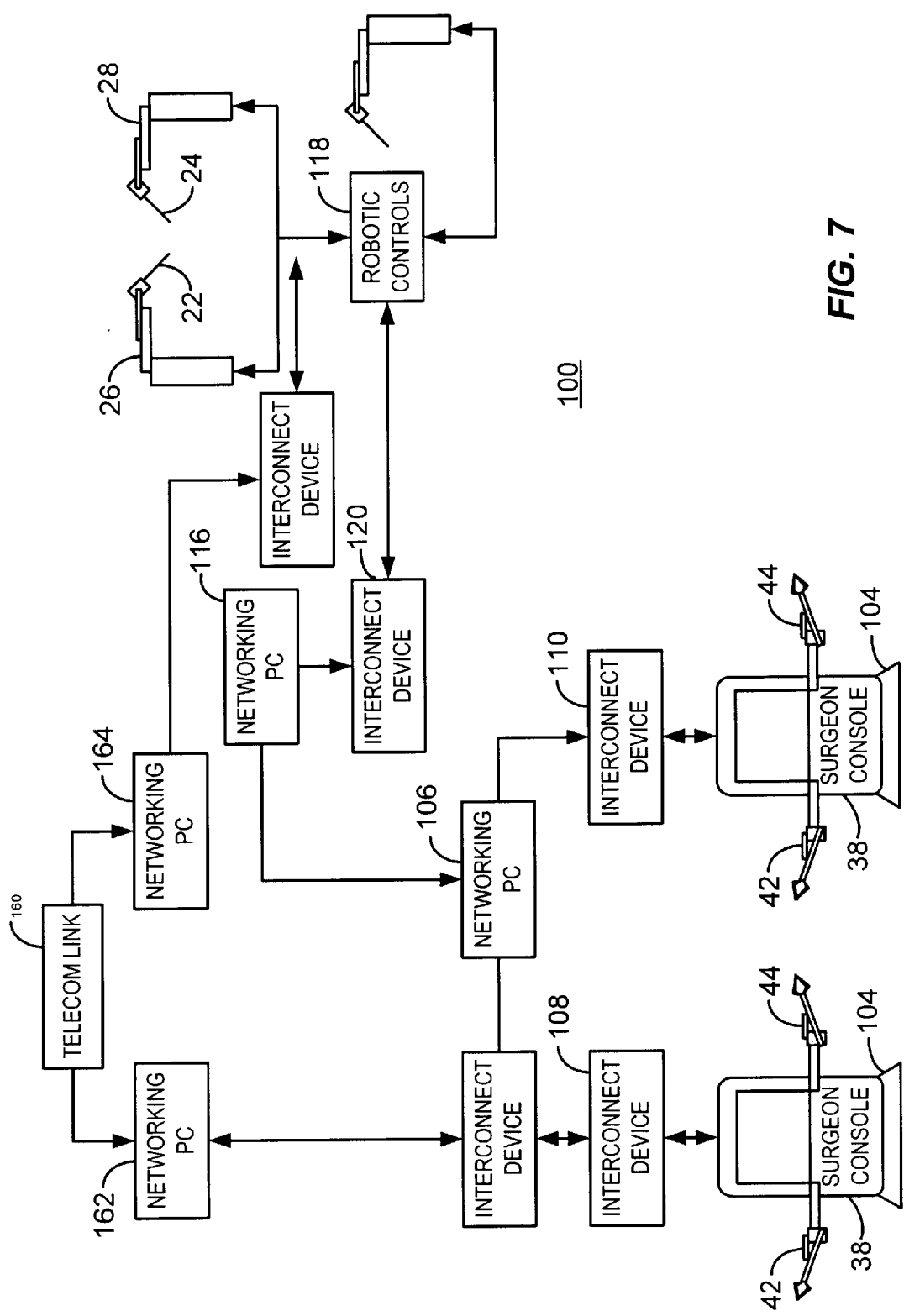
FIG. 7 is an illustration showing an alternate embodiment of the network system.

FIG. 7 shows an alternate embodiment, wherein one or more of the consoles 102 and 104 has an alternate communication link 160. The alternate link may be a telecommunication network that allows the console 102 to be located at a remote location while console 104 is in relative close proximity to the robotic arms, etc. For example, console 102 may be connected to a public phone network, while console 104 is coupled to the controller 118 by a LAN. Such a system would allow telesurgery with the robotic arms, instruments, etc. The surgeon and patient sides of the system may be coupled to the link 160 by network computers 162 and 164.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical system, comprising:
   a first medical device;
   a first input device that can control said first medical device;
   a second input device that can control said first medical device; and
   an arbitrator that is coupled to said first input device and allows either said first input device or said second input device to control said first medical device.

2. The system of claim 1, wherein said first medical device includes a robotic arm.

3. The system of claim 2, wherein said first medical device includes an instrument.

4. The system of claim 1, wherein said first input device includes a console that has a handle.

5. The system of claim 4, wherein said second input device includes a console that has a video screen.

6. The system of claim 1, wherein said second input device includes a touchpad screen.

7. The system of claim 1, wherein said first and second input devices each transmit a packet of information, each packet including a priority that is used by said arbitrator to allow either said first input device or second input device to control said first medical device.

8. The system of claim 1, wherein said first and second input devices each transmit a packet of information, each packet including a source address that is used by said arbitrator to allow either said first input device or second input device to control said first medical device.

9. The system of claim 1, wherein said arbitrator includes a computer.

10. The system of claim 1, further comprising a communication link that couples said first and second input devices with said first medical device.

11. The system of claim 10, further comprising a second medical device that is controlled by a third input device.

12. The system of claim 11, wherein said first medical device includes a robotic arm that moves a medical instrument and said second medical device includes a robotic arm that moves an endoscope coupled to a camera.

13. The system of claim 12, further comprising a communication link that couples said first and second medical devices with said first and second input devices, and a computer that multiplexes robotic data from said robotic arms with video data from said camera onto said communication link.

14. A medical system, comprising:
   a first medical device;
   first input means for controlling said first medical device;
   second input means for controlling said first medical instrument; and,
   arbitrator means for allowing either said first input device or said second input device to control said first medical device.

15. The system of claim 14, wherein said first medical device includes a robotic arm.

16. The system of claim 15, wherein said first medical device includes an instrument.

17. The system of claim 14, wherein said first input means includes a console that has a handle.

18. The system of claim 17, wherein said second input means includes a console that has a video screen.

19. The system of claim 14, wherein said second input means includes a touchpad screen.

20. The system of claim 14, wherein said first and second input means each transmit a packet of information, each packet including a priority that is used by said arbitrator means to allow either said first input means or second input means to control said first medical device.

21. The system of claim 14, wherein said first and second input means each transmit a packet of information, each packet including a source address that is used by said arbitrator means to allow either said first input means or second input means to control said first medical device.

22. The system of claim 14, wherein said arbitrator means includes a computer.

23. The system of claim 14, further comprising communication means for coupling said first and second input means with said first medical device.

24. The system of claim 23, further comprising third input means for controlling a second medical device.

25. The system of claim 24, wherein said first medical device includes a robotic arm that moves a medical instrument and said second medical device includes a robotic arm that moves an endoscope coupled to a camera.

26. The system of claim 25, further comprising communication means for coupling said first and second medical devices with said first and second input means, and multiplexor means for multiplexing robotic data from said robotic arms with video data from said camera onto said communication means.

27. A medical system, comprising:
a first robotic arm;
a first medical instrument coupled to said first robotic arm;
a second robotic arm;
a second medical instrument coupled to said second robotic arm;
a third robotic arm that can hold an endoscope coupled to a camera;
a first console that can control said first and second robotic arms;
a second console that can control said first and second robotic arms;
a first endoscopic input device that can control said third robotic arm;
a second endoscopic input device that can control said third robotic arm; and,
an arbitrator coupled to said first robotic arm, said second robotic arm, said third robotic arm, said first console, said second console, said first endoscopic input device and said second endoscopic input device.

28. The system of claim 27, wherein said first and second consoles each transmit a packet of information including a priority to said arbitrator, said priority is used by said arbitrator to determine whether said first and second robotic arms are to be controlled by either said first console or said second console.

29. The system of claim 27, wherein said first and second consoles each transmit a packet of information including a source address to said arbitrator, said source addresses are used by said arbitrator to determine whether said first and second robotic arms are to be controlled by said first console or said second console.

30. The system of claim 27, further comprising a communication link coupled to said arbitrator and said first and second consoles, said arbitrator multiplexes robotic data from said first, second and third robotic arms with video data from the camera onto said communication link.

31. A medical system, comprising:
a first robotic arm;
a first medical instrument coupled to said second robotic arm;
a second robotic arm;
a second medical instrument coupled to said second robotic arm;
a third robotic arm that can hold an endoscope coupled to a camera;
a first console that can control said first and second robotic arms;
a second console that can control said first and second robotic arms;
a first endoscopic input device that can control said third robotic arm;
a second endoscopic input device that can control said third robotic arm; and,
arbitrator means for allowing said first and second robotic arms to be controlled by either said first console or said second console, and said third robotic arm to be controlled by either said first endoscopic input device or said second endoscopic input device.

32. The system of claim 31, wherein said first and second consoles each transmit a packet of information including a priority to said arbitrator means, said priority is used by said arbitrator means to determine whether said first and second robotic arms are to be controlled by either said first console or said second console.

33. The system of claim 31, wherein said first and second consoles each transmit a packet of information including a source address to said arbitrator means, said source addresses are used by said arbitrator means to determine whether said first and second robotic arms are to be controlled by said first console or said second console.

34. The system of claim 31, further comprising communication means for coupling said arbitrator means with said first and second consoles, said arbitrator means multiplexes robotic data from said first, second and third robotic arms with video data from the camera onto said communication means.

35. A medical system, comprising:
a first medical device;
an arbitrator coupled to said first and second medical devices.

36. The system of claim 35, wherein said arbitrator allows control of said first medical device in accordance with a priority included in a packet of information transmitted to said arbitrator.

37. The system of claim 35, wherein said arbitrator allows control of said first medical device in accordance with a source address included in a packet of information transmitted to said arbitrator.

38. The system of claim 35, wherein said first medical device includes a robotic arm.

39. A medical system, comprising:
a first input device;
a second input device; and,
an arbitrator coupled to said first and second input devices.

40. The system of claim 39, wherein said first input device transmits a first packet of information including a first priority and said second input device transmits a second packet of information including a second priority, said arbitrator transmits either said first or second packet of information based on said first and second priority.

41. The system of claim 39, wherein said first and second input devices each include a console.

42. The system of claim 41, wherein each console includes a pair of handles and a screen.

43. A medical robotic system architecture, comprising:
a communication network that includes an arbitrator;
a robotic arm coupled to said communication network;
a medical instrument coupled to said robotic arm;
a first surgeon console coupled to said communication network; and,
a second surgeon console coupled to said communication network.

44. The architecture of claim 43, wherein said communication network includes an interconnect device.

45. The architecture of claim 43, wherein said first and second consoles each transmit a packet of information, said packet containing a priority field.

46. A medical robotic system architecture, comprising:

a medical instrument coupled to said robotic arm;

movement means for moving said medical instrument;

first surgeon control means for controlling said medical instrument;

second surgeon control means for controlling said medical instrument; and, communication means that includes an arbitrator for coupling said movement means and said medical instrument to said first and second surgeon control means.

47. The architecture of claim 46, wherein said communication means includes an interconnect device.

48. The architecture of claim 46, wherein said first and second control means each transmit a packet of information, said packet containing a priority field.

49. A medical robotic system, comprising:

a medical instrument;

a robotic arm;

a communication network coupled to said robotic arm and said medical instrument;

an input device; and, a computer coupled to said input device, said computer transmits a packet of information over said communication network, said packet including a priority field and a data field that contains robotic data.

50. The system of claim 49, wherein said data field includes RS232 data.

51. The system of claim 49, wherein said input device includes a handle.

52. The system of claim 49, further comprising a screen coupled to said computer.

53. A medical robotic system, comprising:

a medical instrument;

a robotic arm;

a communication network coupled to said robotic arm and said medical instrument;

input means for receiving a command to control said medical instrument; and, transmission means for transmitting a packet of information over said communication network, said packet including a priority field and a data field that contains robotic data that corresponds to the command.

54. The system of claim 53, wherein said data field includes RS232 data.

55. The system of claim 53, wherein said input means includes a handle.

56. The system of claim 53, further comprising a screen coupled to said transmission means.

57. A medical robotic system architecture, comprising:

a communication network;

a robotic arm coupled to said communication network;

a medical instrument coupled to said robotic arm;

a first surgeon console that is coupled to said communication network and transmits a packet of information that includes a priority field; and, a second surgeon console that is coupled to said communication network and transmits a packet of information that includes a priority field.

58. The architecture of claim 43, wherein said communication network includes an interconnect device.

59. A medical robotic system architecture, comprising:

a medical instrument coupled to said robotic arm;

movement means for moving said medical instrument;

first surgeon control means for controlling said medical instrument and transmitting a packet of information that includes a priority field;

second surgeon control means for controlling said medical instrument and transmitting a packet of information that includes a priority field; and, communication means for coupling said movement means and said medical instrument to said first and second surgeon control means.

60. The architecture of claim 46, wherein said communication means includes an interconnect device.

* * * * *